US012708784B2

(12) United States Patent
English

(10) Patent No.: US 12,708,784 B2
(45) Date of Patent: Aug. 18, 2026

(54) IMPLANTABLE MEDICAL DEVICE WITH HYDROGEN GETTER

(71) Applicant: Cardiac Pacemakers, Inc., St. Paul, MN (US)

(72) Inventor: James Michael English, Cahir (IE)

(73) Assignee: Cardiac Pacemakers, Inc.

( * ) Notice: Subject to any disclaimer, the term of this patent is extended or adjusted under 35 U.S.C. 154(b) by 185 days.

(21) Appl. No.: 18/432,553

(22) Filed: Feb. 5, 2024

(65) Prior Publication Data

US 2024/0261579 A1 Aug. 8, 2024

Related U.S. Application Data

(60) Provisional application No. 63/443,564, filed on Feb. 6, 2023.

(51) Int. Cl.
*A61N 1/375* (2006.01)
*H01J 7/18* (2006.01)

(52) U.S. Cl.
CPC ............ *A61N 1/3754* (2013.01); *H01J 7/183* (2013.01); *H01J 7/186* (2013.01)

(58) Field of Classification Search
None
See application file for complete search history.

(56) References Cited

U.S. PATENT DOCUMENTS 4,014,346 A 3/1977 Brownlee et al.
4,254,775 A 3/1981 Langer
4,314,562 A 2/1982 Ware
5,876,424 A 3/1999 O'Phelan et al.
5,999,398 A 12/1999 Makl et al.
6,031,710 A 2/2000 Wolf et al.
6,428,612 B1 8/2002 McPhilmy et al.
6,603,654 B2 8/2003 Rorvick et al.
6,881,516 B2 4/2005 Aamodt et al.
7,194,309 B2 3/2007 Ostroff et al.
7,263,401 B2 8/2007 Scott et al.
7,485,277 B1 2/2009 Shepodd et al.
7,769,457 B2 8/2010 Fonte (Continued)

FOREIGN PATENT DOCUMENTS

EP 2934670 B1 1/2018
WO 2012036944 A1 3/2012

OTHER PUBLICATIONS

Henkel, Presentation, Macromelt Molding, 35 pages, https://www.ellsworth.com/globalassets/literature-library/manufacturer/henkel-loctite/henkel-presentation-technolmelt-formerly-branded-as-macromelt-molding.pdf Accessed Mar. 2, 2020.

(Continued)

*Primary Examiner* — Mallika D Fairchild
(74) *Attorney, Agent, or Firm* — Seager, Tufte & Wickhem LLP

(57) ABSTRACT

Hydrogen getters are provided in active implantable medical device by applying a layer of selected metal with a chosen thickness over an un-oxidized portion of a base metal. The base metal may be titanium, and the selected metal may be palladium or platinum, with a thickness of less than 250 nanometers, where the selected metal acts as a passivation layer relative to oxidation but allows hydrogen capture by the base metal. The getter may be a separate component or may be formed as part of an existing component such as a feedthrough ferrule.

10 Claims, 6 Drawing Sheets

(56) References Cited

U.S. PATENT DOCUMENTS 7,771,838 B1 * 8/2010 He .................... B23K 35/0238
428/670
7,968,226 B2 6/2011 Aamodt et al.
8,065,006 B2 11/2011 Rorvick et al.
8,065,007 B2 11/2011 Ries et al.
8,414,963 B2 * 4/2013 Baillin .................... H01L 23/10
427/97.3
8,463,393 B2 6/2013 Strother et al.
8,774,921 B2 7/2014 Fonte
9,105,899 B2 8/2015 Pakula et al.
9,713,725 B2 7/2017 Bobgan et al.
10,040,021 B2 8/2018 Ries et al.
10,226,055 B2 3/2019 Rothfuss et al.
10,434,316 B2 10/2019 Kelley et al.
10,894,164 B2 1/2021 Strommer et al.
11,247,059 B2 2/2022 Keller et al.
2003/0204216 A1 10/2003 Ries et al.
2005/0245971 A1 11/2005 Brockway et al.
2009/0034769 A1 2/2009 Darley et al.
2010/0305654 A1 12/2010 Fonte
2012/0069536 A1 3/2012 Sporon-Fiedler et al.
2013/0235550 A1 9/2013 Stevenson et al.
2015/0196867 A1 7/2015 Ries et al.
2015/0321013 A1 11/2015 Smith et al.
2016/0151635 A1 6/2016 Frysz et al.
2016/0287865 A1 10/2016 Bobgan et al.
2018/0207427 A1 7/2018 Webb et al.
2019/0168005 A1 6/2019 Li et al.
2019/0321628 A1 10/2019 Stevenson et al.
2020/0054881 A1 2/2020 Frustaci et al.
2020/0121417 A1 4/2020 Prescott et al.
2020/0203881 A1 * 6/2020 Marzano ................ H01G 4/232
2020/0246625 A1 8/2020 Stevenson et al.
2020/0276440 A1 9/2020 Stevenson et al.
2021/0121705 A1 4/2021 Ries et al.
2022/0047876 A1 2/2022 Becklund et al.
2022/0249852 A1 8/2022 Peterson
2022/0288401 A1 9/2022 Landherr et al.

OTHER PUBLICATIONS

International Search Report and Written Opinion dated Nov. 19, 2021 for International Application No. PCT/US2021/045724.

* cited by examiner 100
110
120
102

100
102

100
110
102

IMPLANTABLE MEDICAL DEVICE WITH HYDROGEN GETTER

CROSS REFERENCE TO RELATED APPLICATIONS

The present application claims the benefit of and priority to U.S. Prov. Pat. App. No. 63/443,564, filed Feb. 6, 2023, titled IMPLANTABLE MEDICAL DEVICE WITH HYDROGEN GETTER, the disclosure of which is incorporated herein by reference.

BACKGROUND

A wide variety of active implantable medical devices (AIMD) are known, including pacemakers, defibrillators, neural modulation or stimulation systems, drug pumps, circulation systems, etc. Such devices often include an enclosure or housing, often made of metal and hermetically sealed to contain operational circuitry for the AIMD. Prior to sealing the housing, the gaseous contents thereof are typically evacuated and/or controlled to limit the presence of moisture and hydrogen, among other gasses. Gasses can accumulate or emanate from components in the AIMD housing, and require removal using, for example, desiccants and hydrogen getters. Hydrogen getters can add expense to the AIMD, and require special handling and care. Often a hydrogen getter is provided in the form of a piece of material that is placed within the AIMD canister, such as by attachment to the housing interior, to a circuit board, or another component such as a frame, battery, or capacitor. New and/or alternative ways of providing a hydrogen getter are desired.

OVERVIEW

The present inventor has recognized, among other things, that a problem to be solved is the need for new and/or alternative hydrogen getter solutions. In some examples, a hydrogen getter is constructed as part of a component of the AIMD, such as by processing a ferrule used in an AIMD feedthrough to serve as a hydrogen getter. The ferrule or other component may be made out of titanium, or may have a titanium layer deposited or applied thereon, with a thin layer of a second metal, such as platinum or palladium, applied on the bare titanium in a controlled environment in which oxidation of the titanium is not allowed. The second metal is applied to prevent oxidation of the titanium, and has a thickness that will still allow hydrogen to pass therethrough, allowing the un-oxidized titanium to act as a hydrogen getter.

A first illustrative an non-limiting example takes the form of an implantable medical device comprising: a canister housing operational circuitry for performing functions of the implantable medical device; a hydrogen getter comprising a titanium layer coated with a layer of selected metal having a chosen thickness, the selected metal and chosen thickness being permeable to hydrogen and substantially impermeable to oxygen, preventing oxidation of the titanium layer in the location of the layer of selected metal while allowing hydrogen to pass therethrough.

Additionally or alternatively, the selected metal is palladium, and the chosen thickness is in the range of about 2 nanometers to about 250 nanometers.

Additionally or alternatively, the selected metal is platinum, and the chosen thickness is in the range of about 2 nanometers to about 250 nanometers.

Additionally or alternatively, the canister defines an opening in which a feedthrough assembly resides, and the hydrogen getter is part of a ferrule which surrounds the feedthrough assembly, the ferrule made of titanium and having thereon the layer of selected metal having a chosen thickness is placed.

Additionally or alternatively, the hydrogen getter is formed by removing an oxidation layer from at least a portion of the ferrule, and depositing the selected metal in the selected thickness thereon.

Additionally or alternatively, the selected metal is placed on the portion of the ferrule by vapor deposition.

Additionally or alternatively, the hydrogen getter is formed by applying a layer of titanium to a portion of the ferrule, and depositing the selected metal in the selected thickness onto the layer of titanium.

Additionally or alternatively, the hydrogen getter is attached to a component carried inside the canister.

Additionally or alternatively, the component carried inside the canister includes a titanium layer, and the hydrogen getter is formed by applying the layer of selected metal onto the titanium layer of the component at a location where the titanium layer is not oxidized.

Additionally or alternatively, the hydrogen getter is a discrete component.

Another illustrative and non-limiting example takes the form of a method of manufacturing a ferrule for use in an implantable medical device feedthrough assembly, the implantable medical device comprising a housing, operational circuitry inside the housing, a header attached to the housing, a feedthrough assembly coupling the operational circuitry to a component in the header, and the ferrule, the ferrule configured to surround the feedthrough assembly, the method comprising: starting with the ferrule having an oxidation layer thereon, removing the oxidation layer in a selected area; and depositing in the selected area a selected metal having a chosen thickness, wherein the selected metal and chosen thickness allow hydrogen to pass therethrough while preventing oxidation therethrough.

Additionally or alternatively, the ferrule is made of titanium.

Additionally or alternatively, the selected metal is palladium, and the chosen thickness is in the range of about 2 nanometers to about 250 nanometers.

Additionally or alternatively, the selected metal is platinum, and the chosen thickness is in the range of about 2 nanometers to about 250 nanometers.

Additionally or alternatively, the depositing step is performed by vapor deposition.

Another illustrative and non-limiting example takes the form of a ferrule for use in an implantable medical device having a feedthrough assembly, the ferrule configured to surround the feedthrough assembly, wherein the ferrule has on a portion thereof a layer of selected metal in a chosen thickness to allow the ferrule to serve as a hydrogen getter by preventing oxidation through the layer of selected metal while allowing hydrogen to pass therethrough.

Additionally or alternatively, the ferrule is made of titanium, the selected metal is palladium, and the chosen thickness is in the range of about 2 nanometers to about 250 nanometers.

Additionally or alternatively, the ferrule is made of titanium, the selected metal is platinum, and the chosen thickness is in the range of about 2 nanometers to about 250 nanometers.

Additionally or alternatively, the layer of selected metal in a selected thickness is deposited on the ferrule by removing an oxidation layer from at least the portion of the ferrule, and depositing the selected metal in the chosen thickness thereon.

Additionally or alternatively, the selected metal is placed on the portion of the ferrule by vapor deposition.

Additionally or alternatively, the layer of selected metal in a chosen thickness is positioned over a layer of titanium, the titanium having been deposited onto the ferrule.

Another example takes the form of an implantable medical device comprising a housing, operational circuitry contained in the housing, a header attached to the housing, a feedthrough assembly coupling the operational circuitry to the header, and the ferrule of as described in the preceding ferrule examples.

Another illustrative and non-limiting example takes the form of a method of manufacturing a ferrule for use in an implantable medical device feedthrough assembly, the implantable medical device comprising a housing, operational circuitry inside the housing, a header attached to the housing, a feedthrough assembly coupling the operational circuitry to a component in the header, and the ferrule, the ferrule configured to surround the feedthrough assembly, the method comprising: starting with the ferrule having an oxidation layer thereon, applying a layer of titanium in a selected area; and depositing on the layer of titanium in the selected area a selected metal having a chosen thickness, wherein the selected metal and chosen thickness allow hydrogen to pass therethrough while preventing oxidation therethrough.

Additionally or alternatively, the selected metal is palladium, and the chosen thickness is in the range of about 2 nanometers to about 250 nanometers.

Additionally or alternatively, the selected metal is platinum, and the chosen thickness is in the range of about 2 nanometers to about 250 nanometers.

Additionally or alternatively, the depositing step is performed by vapor deposition.

This overview is intended to provide an introduction to the subject matter of the present patent application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
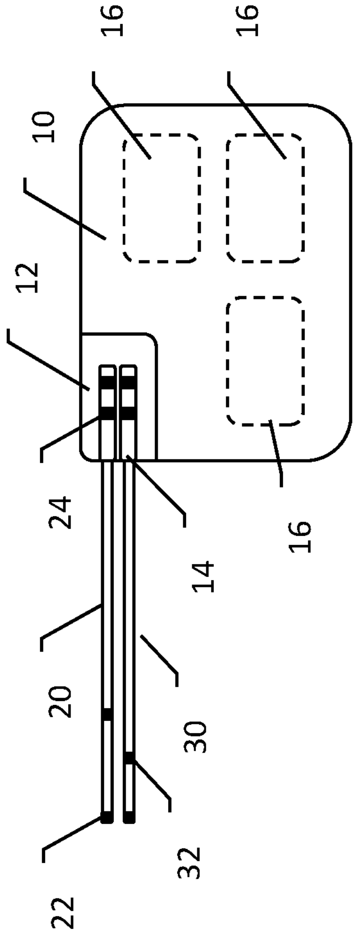
FIG. 1 shows a generic active implantable medical device.

FIG. 1 shows a generic active implantable medical device (AIMD). A housing 10 is shown with a header 12 having ports 14 for receiving one or more leads 20, 30. The housing 10 contains therein various operational circuitry 16, shown as several modules, which may include a power supply, such as a battery, therapy output circuitry, telemetry circuitry, a controller or processor, memory, analysis circuitry, sensing circuitry, etc. Circuitry may include a wide variety of memory, logic, amplifiers, transistors, resistors, inductors, capacitors, filters, etc. The lead or leads 20, 30 may comprise electrodes 22, 32, though other features may be present such as optical outputs, transducers (ultrasound for example), or ports such as for a drug or insulin pump. A wide variety of such products are known and commercially available, such as the range of pacemakers, defibrillators, spinal cord stimulators and deep brain stimulators available from Boston Scientific Corporation and Medtronic various drug pumps and insulin pumps from various manufacturers, or vagus nerve stimulators available from Cyberonics, etc.

AIMDs may be, for example and without limitation, implantable pacemakers, defibrillators, cardiac monitors, cardiac resynchronization therapy devices, cardiac assist devices neurostimulators, neuromodulators, spinal cord stimulators, Vagus nerve stimulators, deep brain stimulation systems, sacral nerve stimulators, drug or therapeutic delivery systems (drug pumps) or other systems. Some modules 16 may store a therapeutic substance, such as a drug, if the AIMD is a drug pump, or insulin, if the AIMD is an insulin source, which may be refillable via a port.

As used herein, an AIMD can be any implantable device for which a hydrogen getter is useful. Most such devices will have an enclosure, such as housing 10 that is hermetically sealed. The AIMD header 12 is used to provide a location for attaching the cannulas or leads 20, 30 to ports 14, and also to protect the housing 10 from ingress of bodily fluids. A lead may serve for example in an electrical stimulus system, and a cannula may be used for a drug pump; items 20 and 30 may be either. A leadless system may also be used. The port 14 can be provided using a feedthrough assembly in the AIMD header 12, as further described below. For example, in an electrical stimulator, the ports 14 may 14 may comprise contacts that interact with contacts 24 on the lead 20, for example, providing electrical or other connection between element 22 and the modules 16 of the operational circuitry in the housing 10.

Figure 2:
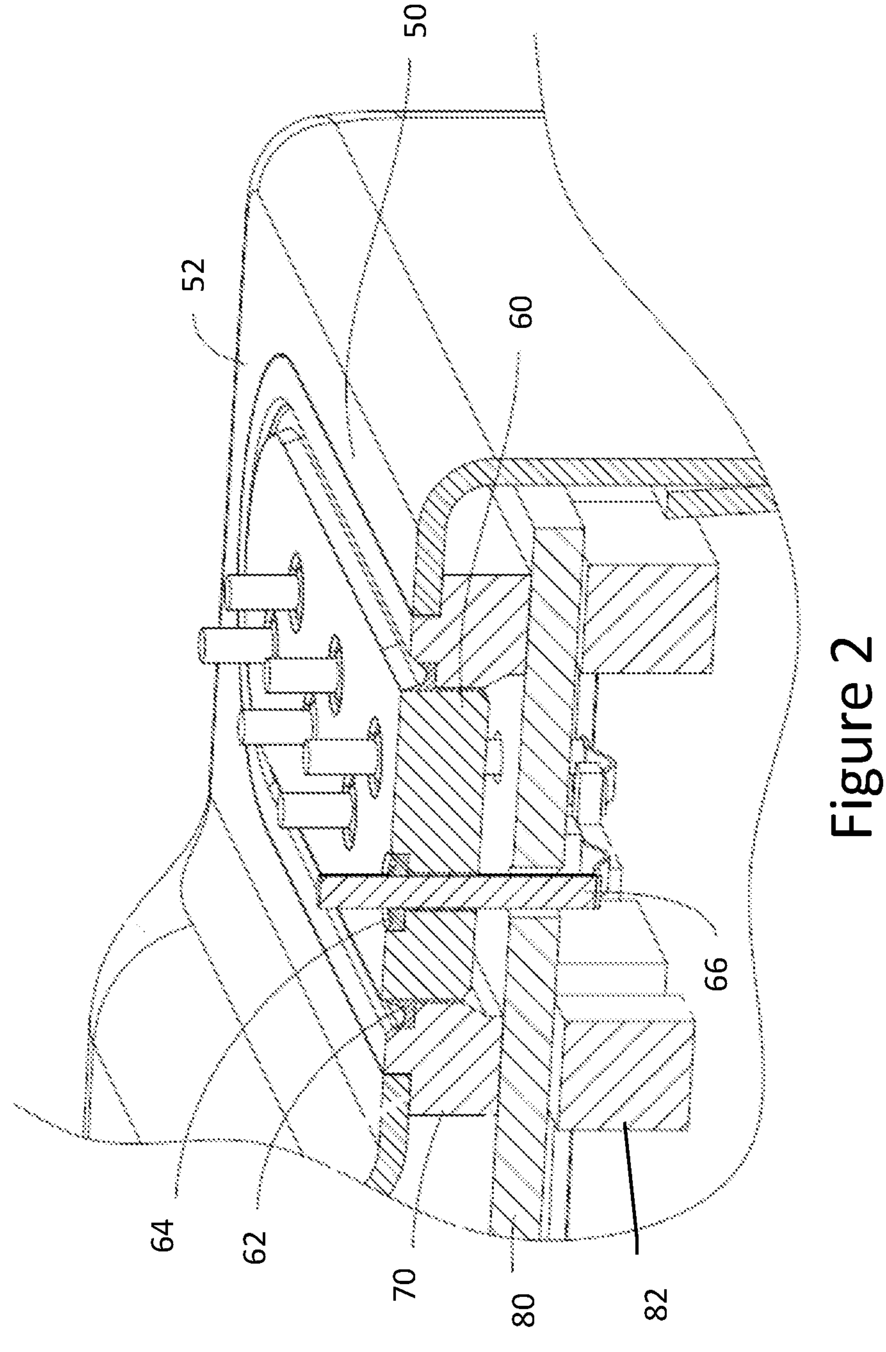
FIG. 2 illustrates a feedthrough assembly for an active implantable medical device.

FIG. 2 illustrates a feedthrough assembly for an active implantable medical device. In this example the housing 50 includes a header region 52, shown here as a side-mount header region 52, in which the header 50 has an opening; other designs may be used. A feedthrough dielectric 60 is provided having a plurality of holes through which feedthrough wires or pins 66 pass. The feedthrough dielectric 60 is surrounded by a ferrule 70, which may be welded to the housing 50. In an example, the housing and the ferrule 70 are both made of titanium. Braze preforms 62, 64 seal the gaps between the ferrule 67 and the feedthrough dielectric 60, as well as around the feedthrough pins 66. Adhesive or welding may instead by used to seal such gaps and secure the componentry together. The feedthrough pins 66 couple to electronics 82 within the housing 50, carried on a circuit board 80.

The feedthrough pins 66 couple to electrical connectors or other systems (a magnetic coil used for telemetry and/or battery charging, or an RF antenna, for example) in the header, and also to the circuitry 82 inside the housing 50. For example, the feedthrough pins 66 may couple to connectors in the header ports, which in turn electrically interact with electrical contacts on the end of a lead inserted therein. The dielectric 60 is used to provide electrical separation between the feedthrough pins 66, which may also have their own insulators if desired. In some examples, the ferrule 70 is of a same or weld-compatible material as the housing 50. For example, both may be made of titanium. In some examples, the housing 50 may be made of titanium having a titanium-nitride coating or layer, as desired.

Titanium is highly reactive with oxygen, and forms a thin, impermeable oxidation layer thereon when exposed to oxygen. Titanium is also reactive with hydrogen and other gasses, however, the oxidation layer that forms during oxygen exposure is impermeable to those other gasses, making titanium having an oxidation layer thereon unusable as a hydrogen getter. In some examples herein, titanium that is already present in an AIMD is used as a hydrogen getter by first treating the titanium to prevent oxidation in a way that retains the ability to act as a hydrogen getter. In other examples, discrete titanium getters are formed and then placed in an AIMD by coating an un-oxidized portion of the titanium, or a portion thereof, to prevent the impermeable oxidation.

Figure 3:
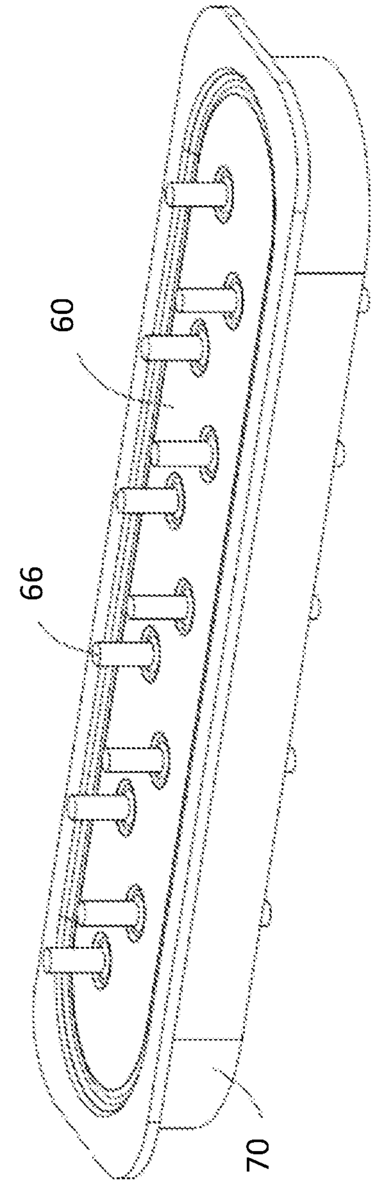
FIG. 3 shows an illustrative feedthrough.

FIG. 3 shows an illustrative feedthrough in isolation. As can be seen, the ferrule 70 surrounds the dielectric 60, having the feedthrough pins 66 passing therethrough. On a portion of the ferrule, a hydrogen getter has been formed at 90. The hydrogen getter at 90 may be formed by, for example, applying heat, such by high temperature plasma arc, etching, chemical processing, or mechanical removal of the oxide layer in an oxygen-free environment (understood to mean a low oxygen or zero oxygen environment, as desired). The exposed bare titanium is then coated, such as by vapor deposition, with a second material, such as a metal which may be, for example and without limitation, palladium or platinum. The second material may be applied in a relatively thin layer, such as in the range of about 1 to about 250 nanometers, or about 2 to about 150 nanometers, or about 5 to about 100 nanometers, as desired. Within these ranges various design tradeoffs are present. For example, thicker deposited layers may be more durable and less prone to damage during handling and manufacturing, though thicker layers may also be more expensive and time consuming to apply, and may slow hydrogen update therethrough, in comparison with thinner layers. In some examples, the second material may be applied with varying thickness, if desired, to provide higher hydrogen absorption rates in a short term via a first portion with thinner second material, while also having a second portion with a thicker second material layer for longer term capability at lower absorption rates, to account for residual out-gassing early in device life. Other examples may have a single thickness for the second material.

In another example, the hydrogen getter 90 is constructed by vapor deposition or other deposition process, in an oxygen-free environment, a layer of titanium onto the ferrule 70, and then to apply the second material to the bare titanium surface. When a titanium layer is deposited on the ferrule 70, the ferrule 70 may be made of any material that is compatible with such deposition, including, for example and without limitation, stainless steel, gold, silver, etc.; if needed a tie layer or "primer" layer may be provide to ensure adhesion between an applied titanium layer and the ferrule 70.

The ferrule 70, in this example, provides a stable surface on a component which is very compatible with high temperature processes, but it is not necessary for the ferrule 70 to be used in this way. Other components may be used instead.

In other examples, rather than creating the getter 90 on the ferrule 70, the getter 90 may be placed on another component in the system, such as on a heat sink, on a circuit board, on an inner surface of the housing, on a frame that is used within the housing to secure components in place, on a component of the operational circuitry 16 (FIG. 1), such as on a battery or capacitor for example, or elsewhere on any component in the device. When a component is chosen for this use, it may be desirable to select a component which will be compatible with the deposition process, and which is itself stable enough to avoid the getter 90 being damaged. For example, a battery cell external housing may be used, as long as the portion of the battery cell that is used will not swell (as is known to happen with certain battery types commonly used in AIMDs) over time in a way that would cause flaking or other damage to the getter 90. Placement on a housing may create stresses over time; if desired, an intermediate layer between the titanium and the housing itself may be provided to absorb such stresses to prevent cracking of the housing or the getter.

Figure 4C:
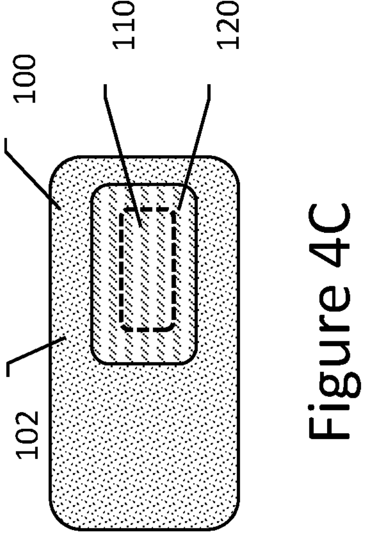
FIGS. 4A-4C show in graphic form a method of creating a hydrogen getter.
Figure 4A:
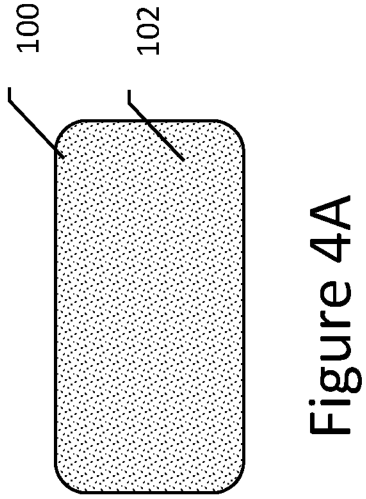
Figure 4B:
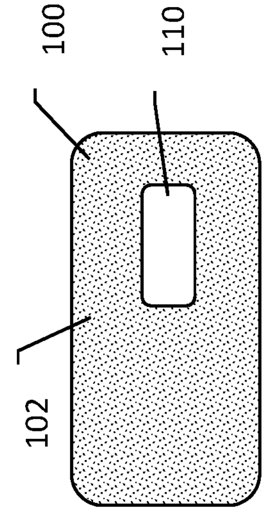

FIGS. 4A-4C show in graphic form a method of creating a hydrogen getter. FIG. 4A shows a component 100 that is to be used as the hydrogen getter. The component 100 may be formed of titanium, and has thereon a titanium oxidation layer 102. The component 100 may be, for example and without limitation, a ferrule used in a feedthrough assembly, though any other suitable component of the AIMD may be used. In the alternative, the component 100 may be a blank or disc made of titanium, insertable to the AIMD as a discrete getter.

At FIG. 4B, the component 100 has been treated, such as by etching, grinding, or heat treatment, including plasma heating, to create an area of bare titanium at 110. Laser or chemical treatment may be used instead or in addition to any such removal processes. While a relatively small area is shown at 110, it should be understood that a larger area, one or more entire surface faces, or the entire surface of component 100 may be made bare as desired. The area of bare titanium may be in the range of, for example and without limitation, one square millimeter up to several square centimeters. In some examples, the area of bare titanium is in the range of about 10 square millimeters up to 100 square millimeters (one square centimeter).

In FIG. 4C, a layer 120 of a selected material having a chosen thickness has been applied over the bare area 110. The selected material and chosen thickness are determined in accordance with their ability to both block oxidation of the area of bare titanium 110 and to allow hydrogen to permeate therethrough and be absorbed by the bare titanium 110. For example, palladium or platinum may be used as the layer 120, with a thickness in the range of about 1 nanometer (nm) to about 250 nm, or more or less. For example, the thickness may be about 1 to about 250 nm, about 5 to about 100 nm, or about 10 to about 50 nm, where "about" indicates a range of +/−10%.

Palladium or platinum are two metals which may be used in layer 120, which may also be referred to as a passivation layer as it prevents at least one source of corrosion (oxygen) from interacting with the underlying titanium. Other metals can also be used. A linking layer or adhesive may be applied to the bare titanium, if desired, to enhance mechanical coupling therebetween. Rather than a metal, a polymer or non-metal may be used, if desired. For example, a layer of oxygen impermeable material may be applied, where the material can be any of a metal, or a non-metal material such as a polymer. A blend of two or more materials may be used if desired.

Figure 5:
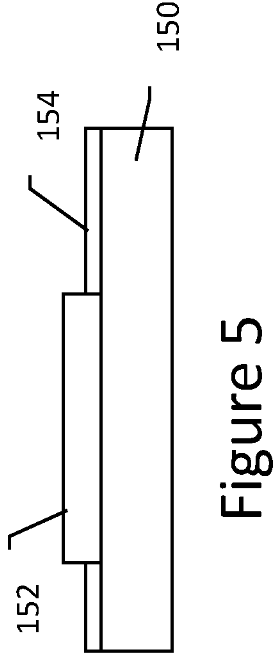
FIGS. 5 and 6 show, in side view, hydrogen getters.
Figure 6:
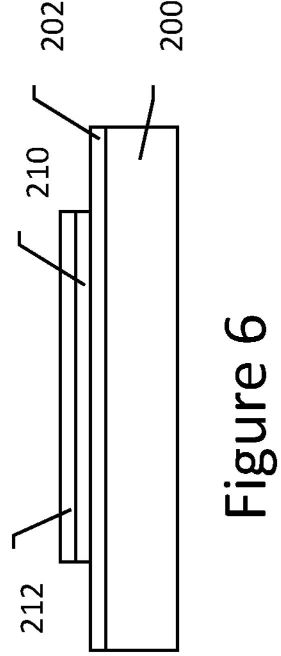

FIGS. 5 and 6 show, in side view, hydrogen getters. Starting with FIG. 5, a base layer 150, which may be formed of titanium, has thereon an oxidation layer 154. A passivation layer is shown at 152 of a second material, such as palladium or platinum. The passivation layer 152 prevents oxidation of the underlying base layer 150, but is formed of a material that is permeable to hydrogen, and is deposited in a thickness that will allow hydrogen to pass therethrough, and interact with the base layer 150. As described above, the passivation layer 152 may be applied after a portion of the oxidation layer 154 has been removed, or may be applied to a selected region of the base layer 150 with the base layer 150 entirely bare, after which the oxidation layer 154 later forms.

FIG. 6 shows another getter. Here, the base layer 200 may be of any suitable material, with or without an oxidation layer 202 thereon. A region of a getter material, such as a titanium, is applied at 210, over which the passivation layer 212 is placed. The passivation layer may be palladium or platinum, or other material as noted previously, and has a chosen thickness allowing hydrogen permeation.

Figure 8:
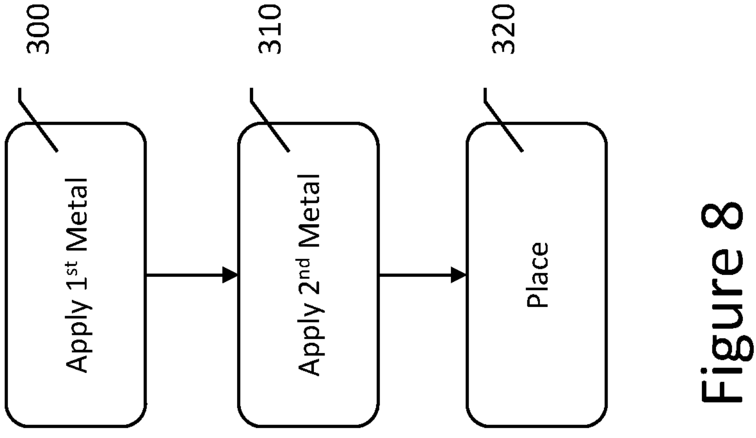
FIGS. 7-8 are block flow diagrams for making and placing hydrogen getters.
Figure 7:
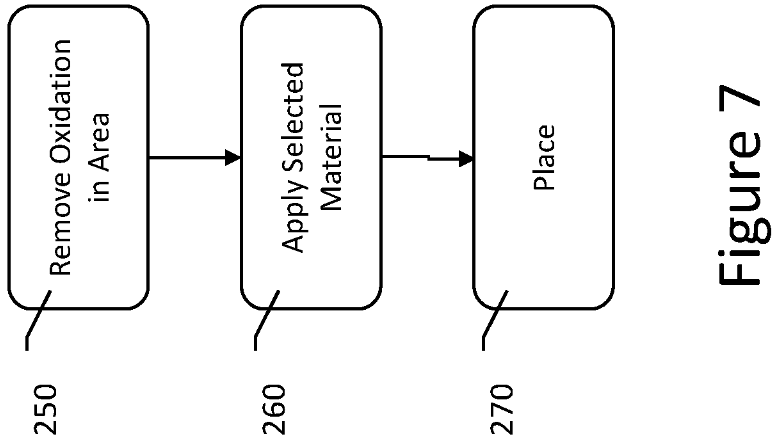

FIGS. 7-8 are block flow diagrams for making and placing hydrogen getters. FIG. 7 shows an example in which the method starts at 250 with removing oxidation in an area. Step 250 may be applied to the entire surface of an object, or to only a portion thereof, as desired. Step 250 may be performed by chemical etching, mechanical removal (cutting, grinding, etc.), electrochemical process, or the application of heat, electricity or light energy, as desired. A selected second material is then applied, as indicated at 260, over the area in which oxidation has been removed. The resulting product is then placed appropriately, whether by placing a component into position in a pulse generator, or by placing a discrete getter at a desired location in an implantable device.

In a more particular example, block 250 may be performed by removing titanium oxide from at least a portion of a titanium ferrule used in a pulse generator feedthrough. A selected material, such as palladium or platinum, is then applied to the area where the oxidation was removed in a chosen thickness, such as 1 nm to 250 nm of thickness, at block 250. Finally, the ferrule is positioned and secured in place in the feedthrough area of an implantable pulse generator.

FIG. 8 shows another example. Here, at block 300 a desired first metal is applied to a component of an AIMD. A second metal is then applied at block 310 over at least a portion, or all, of the first metal. The component is then placed as indicated at 320. In a more specific example, block 300 is performed by plasma vapor deposition of a layer of titanium to a component of an AIMD, such as a feedthrough ferrule. The layer of titanium may have a thickness of about 100 nanometers to about 1 millimeter, or more or less. Layers in the range of a few micrometers (1 to 10 micrometers) may be useful, for example. Block 310 is then performed by plasma vapor deposition of a selected material, such as palladium or platinum, onto the deposited layer of titanium, in a thickness of about 1 nm to 250 nm.

Each of these non-limiting examples can stand on its own, or can be combined in various permutations or combinations with one or more of the other examples. The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. An implantable medical device comprising:

a canister housing operational circuitry for performing functions of the implantable medical device;

a hydrogen getter comprising a titanium layer coated with a layer of selected metal having a chosen thickness, the selected metal and chosen thickness being permeable to hydrogen and substantially impermeable to oxygen, preventing oxidation of the titanium layer in the location of the layer of selected metal while allowing hydrogen to pass therethrough.

2. The implantable medical device of claim 1, wherein the selected metal is palladium, and the chosen thickness is in the range of about 2 nanometers to about 250 nanometers.

3. The implantable medical device of claim 1, wherein the selected metal is platinum, and the chosen thickness is in the range of about 2 nanometers to about 250 nanometers.

4. The implantable medical device of claim 1 wherein the canister defines an opening in which a feedthrough assembly resides, and the hydrogen getter is part of a ferrule which surrounds the feedthrough assembly, the ferrule made of titanium and having thereon the layer of selected metal having a chosen thickness is placed.

5. The implantable medical device of claim 4, wherein the hydrogen getter is formed by removing an oxidation layer from at least a portion of the ferrule, and depositing the selected metal in the selected thickness thereon.

6. The implantable medical device of claim 5 wherein the selected metal is placed on the portion of the ferrule by vapor deposition.

7. The implantable medical device of claim 4, wherein the hydrogen getter is formed by applying a layer of titanium to a portion of the ferrule, and depositing the selected metal in the selected thickness onto the layer of titanium.

8. The implantable medical device of claim 1, wherein the hydrogen getter is attached to a component carried inside the canister.

9. The implantable medical device of claim 8, wherein the component carried inside the canister includes a titanium layer, and the hydrogen getter is formed by applying the layer of selected metal onto the titanium layer of the component at a location where the titanium layer is not oxidized.

10. The implantable medical device of claim 8, wherein the hydrogen getter is a discrete component.

* * * * *